United States Patent [19]

Satomura et al.

[11] Patent Number: 5,677,194
[45] Date of Patent: Oct. 14, 1997

[54] PROCESS FOR RAPID MEASUREMENT OF TRACE COMPONENTS

[75] Inventors: Shinji Satomura; Hideo Katoh; Kenji Nakamura; Kazunari Hirayasu, all of Amagasaki, Japan

[73] Assignee: Wako Pure Chemical Industries, Ltd., Osaka, Japan

[21] Appl. No.: 309,967

[22] Filed: Sep. 20, 1994

Related U.S. Application Data

[63] Continuation of Ser. No. 796,190, Nov. 22, 1991, abandoned.

[30] Foreign Application Priority Data

Nov. 29, 1990 [JP] Japan ................................. 2-335501

[51] Int. Cl.$^6$ ..................... G01N 33/53; G01N 33/536; G01N 33/537; G01N 33/538
[52] U.S. Cl. ..................... 436/501; 435/7.92; 435/7.93; 435/7.94; 436/530; 436/536; 436/538; 436/539; 436/540; 436/541; 436/805; 436/824; 436/827
[58] Field of Search ............... 435/6, 7.92, 7.93, 435/7.94; 436/518, 530, 531, 536, 538, 539, 540, 541, 805, 827, 824, 501; 210/650, 651

[56] References Cited

U.S. PATENT DOCUMENTS

| 4,298,689 | 11/1981 | Doyle et al. ........................ 436/827 |
| 4,371,515 | 2/1983 | Chu ..................................... 436/544 |
| 4,508,829 | 4/1985 | Sulitzeanu ........................... 436/827 |
| 4,666,866 | 5/1987 | Krauth ................................ 436/538 |
| 4,792,527 | 12/1988 | Uchida et al. ....................... 436/827 |
| 4,865,997 | 9/1989 | Stoker ................................. 436/538 |
| 4,868,131 | 9/1989 | Hiratsuka .......................... 435/7.93 |
| 4,912,034 | 3/1990 | Kalra et al. ......................... 436/518 |
| 4,948,726 | 8/1990 | Longoria ............................. 435/14 |
| 4,952,519 | 8/1990 | Lau ..................................... 436/541 |
| 4,960,692 | 10/1990 | Lentrichia et al. ................. 435/7.93 |
| 5,077,198 | 12/1991 | Shih et al. .......................... 436/538 |

FOREIGN PATENT DOCUMENTS

| A-0 233 385 | 8/1987 | European Pat. Off. . |
| A-0 268 296 | 5/1988 | European Pat. Off. . |
| A-0 357 869 | 3/1990 | European Pat. Off. . |
| WO 87/03690 | 6/1987 | WIPO . |
| WO 90/09588 | 8/1990 | WIPO . |

OTHER PUBLICATIONS

Takahashi, T. "Methods of Hybridization in Solution (Part I)" *Bio Industry*, 7(4):46–52 (1990).
Takahashi, T. "Methods of Hybridization in Solution (Part II)" *Bio Industry* 7(5):45–54 (1990).
(Abstract Only) AU-A-68276/87, Australian Patent Abstract (Aug. 27,1987).
Clinical Chemistry, 30, pp. 417–420,1494–1498 (1984).
J. Virological Methods, 15, pp. 109–120 (1987).
J. Immunological Methods, 119, pp. 35–43 (1989).
Clinical Chemistry, 31(9), pp. 1427–1431 (1985).
Millipore Catalogue & Purchasing Guide, 1982, pp. 55–58.

Primary Examiner—Christopher L. Chin
Attorney, Agent, or Firm—Armstrong, Westerman, Hattori, McLeland & Naughton

[57] ABSTRACT

Trace components in samples can be measured rapidly with high precision by applying interaction between an analyte to be measured and an affinity substance and using a membrane having specific separating capability.

10 Claims, 5 Drawing Sheets

F I G. 5
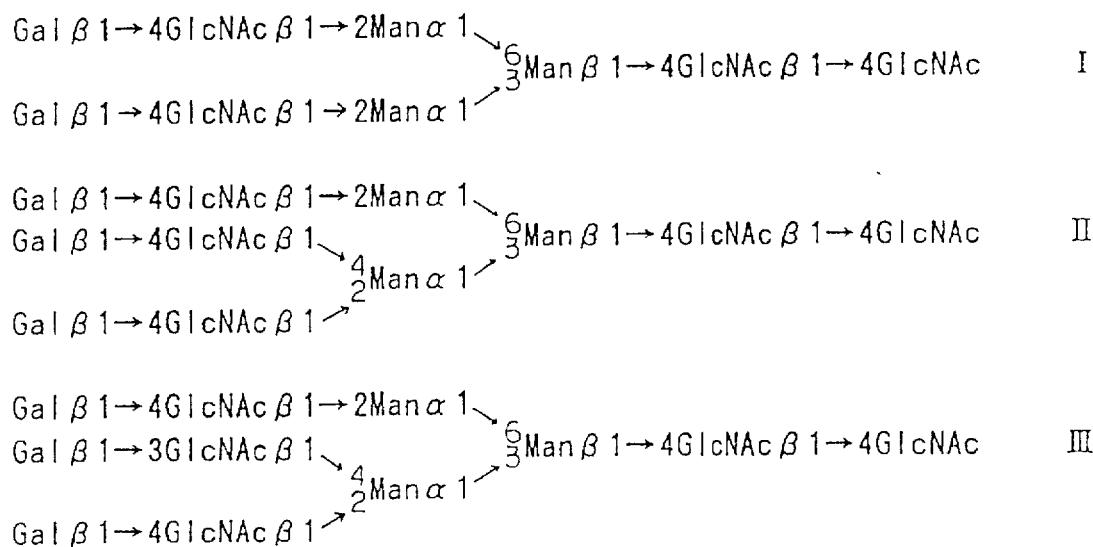

F I G. 6
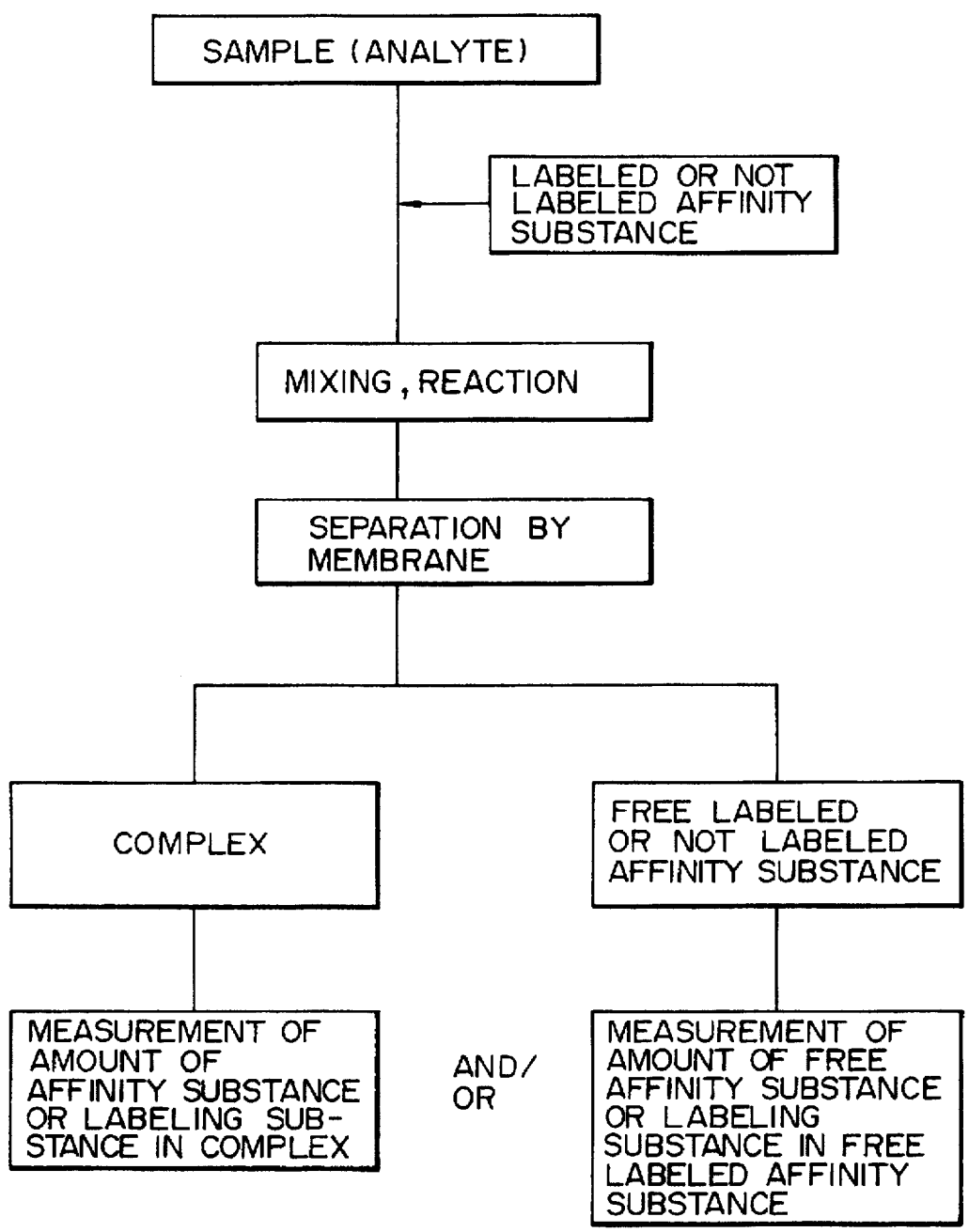

PROCESS FOR RAPID MEASUREMENT OF TRACE COMPONENTS

This application is a continuation of application Ser. No. 07/796,190, filed Nov. 22, 1991, now abandoned.

BACKGROUND OF THE INVENTION

This invention relates to a process for rapid, easy, and high-precision measurement of trace components in samples derived from living bodies, for example, body fluids such as serum, blood, plasma and urine, or the amount or interaction (or affinity) activity of a substance having specific affinity.

It is known that specific substances interact on each other (namely, they have a high affinity for each other) to form a complex. The specific substances include, for example, the following combinations: antigen and antibody; protease and its protein protease inhibitor; saccharide and lectin; enzyme and substrate therefor or coenzyme; physiologically active substance such as hormone, and receptor or transport protein for said active substance; and a pair of polynucleotide chains of duplex DNA. There are widely employed methods in which trace components in samples are purified or assayed by utilizing the above interaction.

Typical examples of methods for measuring a trace component in a sample by utilizing the above interaction are a method in which an equilibrium state which results from the interaction between an analyte to be measured and a substance having affinity for the analyte (hereinafter abbreviated as "affinity substance") is measured using a labeling substance, whereby the trace component is measured. More specific examples are radioimmunoassay (RIA), enzyme immunoassay (EIA) and fluoroimmunoassay (FIA).

In more detail, the methods for measuring trace components by measuring the equilibrium state which results from the interaction are roughly divided into the following two categories: so-called non-competitive reaction methods which comprise reacting an affinity substance labeled with a labeling substance (hereinafter abbreviated as "labeled affinity substance") with an analyte to be measured, determining the amount of the labeling substance in the resulting complex of the analyte and the affinity substance (hereinafter abbreviated as "complex"), and thereby determining the amount of the analyte; and so-called competitive reaction methods which comprise reacting an analyte to be measured with the analyte which has been labeled with a labeling substance (hereinafter abbreviated as "labeled analyte") and an affinity substance, determining the amount of the labeling substance in the resulting complex of the labeled analyte and the affinity substance (hereinafter abbreviated as "labeled complex"), and thereby determining the amount of the analyte. The methods of each category can be further divided into so-called homogeneous methods in which measurement is carried out without separating the complex formed by the interaction from free (uncomplexed) labeled affinity substance (or labeled analyte), and so-called heterogeneous methods in which measurement is carried out after separating the complex formed by the interaction from free (uncomplexed) labeled affinity substance (or labeled analyte).

In the homogeneous method, the equilibrium state which results from the interaction is measured by utilizing the phenomenon that a labeling substance is activated (or inactivated) by the formation of the complex. Therefore, a measuring procedure and the like in this method are simple, but this method is disadvantageous, for example, in that the kinds of usable labeling substance and analyte to be measured are limited. Accordingly, this method is not widely used.

In the heterogeneous method, various labeling substances can be used and substances in wide variety can be measured. Therefore, this method is a leading method for measuring a trace component. In the heterogeneous method, a procedure of separating the complex (Bound form) formed by the interaction from free (uncomplexed) labeled affinity substance (or labeled analyte) (Free form), i.e., a procedure of the so-called B/F separation, is indispensable. For example, in a measuring method utilizing an antigen-antibody reaction, the B/F separation has been carried out, for example, by solid phase technique comprising combining the complex formed by the interaction with an antibody against either the analyte or affinity substance constituting the complex, which has been immobilized on an insoluble carrier, and then separating the complex combined with the antibody, together with the insoluble carrier; or double antibody technique comprising adding, after completion of the reaction of the analyte with an antibody thereto (a first antibody), an antibody against the first antibody (a second antibody) to the reaction solution to form a new complex with said complex, and separating the thus formed complex as precipitate. Therefore, the heterogeneous method is disadvantageous, for example, in that it requires a troublesome procedure, requires a long time before measurement, and does not permit easy automation of measurement. Accordingly, its improvement is desirable.

In order to solve the above problems in the heterogeneous method, there have been proposed methods in which the B/F separation is carried out by a so-called affinity chromatography which uses a column packed with a carrier on which an analyte to be mesured or an affinity substance for the analyte has been immobilized (Clinical Chemistry, 30, 417–420 (1984); Clinical Chemistry, 30, 1494–1498 (1984); etc.).

However, in these methods, free labeled affinity substance (or labeled analyte) is removed using an affinity chromatography column having the analyte (or the affinity substance) immobilized thereon. Therefore, these methods involve, for example, the following problems: the analyte (or the affinity substance) should be previously prepared (obtained) in a relatively large amount; a packing for the affinity chromatography column should be prepared; an affinity chromatography column suitable for each analyte to be measured is needed; and said column should be regenerated when a large number of samples are dealt with. Accordingly, said methods are not always satisfactory enough.

As a method which can solve the above problems in the methods using an affinity chromatography column, there has been proposed a method which comprises reacting an analyte to be measured with an affinity substance, in a liquid phase to form a complex, and then carrying out the B/F separation by a high pressure liquid chromatography (HPLC) (European Patent Application A1 0357869).

In such a method, the reaction of the analyte with the affinity substance proceeds in a liquid phase and hence is a homogeneous reaction. Therefore, the method is advantageous, for example, in that the reaction time is short, that the reproducibility of measurement is high, and that the procedure is simpler than that of the method using an affinity chromatography column. However, the method involves, for example, the following problems: it takes several (tens of minutes) to deal with one sample; a large number of samples cannot be dealt with at the same time; and when the binding strength between the analyte and the affinity substance is low, the complex is dissociated into the analyte and the affinity substance in the course of separation of the complex by use of a column, so that accurate measurement cannot be carried out. Therefore, there is a desire to seek further improvement in the method.

On the other hand, as measuring methods utilizing separation by use of a membrane, the following methods have been disclosed: a method of reacting an antigen with an antibody, in a liquid phase to form an insoluble complex, and separating the insoluble complex from a solution by use of a membrane filter (Australian Patent Laid-Open No. 68276/87), a method of hybridizing a nucleic acid with a probe in a solution, and then immobilizing the hybrid on a solid carrier, followed by filtration (BIO INDUSTRY, 7, 282–288 (1990); BIO INDUSTRY, 7, 347–356 (1990)), a method of immobilizing cells or DNA on a plate equipped with a filter, reacting the cells or DNA with an affinity substance, and then separating the thus formed complex with the affinity substance by filtration (J. Virological Methods, 15, 109–120 (1987)), and a method of immobilizing an affinity substance (e.g. an antibody) on a membrane, passing a fluid containing an analyte to be measured (e.g. an antigen) through the membrane to form a complex, and thereby separating the analyte (J. Immunological Methods, 119, 35–43 (1989); Clim. Chem., 31, 1427–1431 (1985), European Patent Laid-Open No. 233,385).

SUMMARY OF THE INVENTION

This invention was made in consideration of such conditions and is intended to provide a process which permits very rapid, easy, and high-precision separation and measurement of trace components in samples by means of the interaction between an analyte to be measured and an affinity substance.

This invention provides a process for measuring the amount of an analyte in a sample which comprises mixing a sample containing an analyte to be measured with an affinity substance having affinity for the analyte, either labeled or not with a labeling substance; reacting the analyte with the affinity substance; separating the resulting complex of the analyte and the affinity substance which is in a dissolved state in a solution, from free affinity substance by use of a membrane having specific separating capability; and measuring the amount of the labeling substance or the amount of the affinity substance in the resulting complex.

This invention further provides a process for measuring the amount of an analyte in a sample which comprises mixing a sample containing an analyte to be measured with the analyte which has been labeled with a labeling substance and a substance having affinity for the analyte; reacting the unlabeled analyte and the labeled analyte with the affinity substance; separating the resulting labeled complex of the labeled analyte and the affinity substance which is in a dissolved state in a solution, from free labeled analyte by use of a membrane having a specific separating capability; and measuring the amount of the labeling substance in the resulting complex or the amount of the labeling substance in the free labeled analyte.

This invention still further provides a process for separating a complex of an analyte to be measured and a substance having affinity for the analyte from free affinity substance, which comprises separating the complex dissolved in a solution from free affinity substance by using a membrane having specific separating capability; said complex being formed by mixing a sample containing the analyte with the affinity substance either labeled or not with a labeling substance, and reacting the analyte with the affinity substance.

This invention still further provides a process for separating a labeled complex of an analyte to be measured which has been labeled with a labeling substance and a substance having affinity for the analyte from free labeled analyte, which comprises separating the labeled complex dissolved in a solution from free labled analyte by using a membrane having specific separating capability, said labeled complex being formed by mixing a sample derived from a living body and containing the analyte with the labeled analyte and the affinity substance, and reacting the unlabeled analyte and the labeled analyte with the affinity substance.

BRIEF DESCRIPTION OF THE DRAWINGS

FIG. 5 shows the structure of a labeled oligosaccharide.

FIGS. 6 and 7 are flow sheets explaining processes of the present invention.

DESCRIPTION OF THE PREFERRED EMBODIMENTS

The present inventors earnestly investigated a method for very rapid, easy, and high-precision measurement of trace components in samples by means of the interaction between an analyte to be measured and an affinity substance. In the investigation, it was found that the separation of a complex (or a labeled complex) dissolved in a solution (Bound form) formed by said interaction from free affinity substance (or free labeled analyte) (Free form), i.e., the so-called B/F separation can easily be carried out using a membrane having specific separating capability. It was further found that the amount of an analyte to be measured in a sample can be determined rapidly and easily with high precision by carrying out the B/F separation by use of the membrane, and then measuring the amount of the labeling substance or the affinity substance in the complex, or measuring the amount of the labeling substance in the labeled complex or the amount of the labeling substance in free labeled analyte. Thus, this invention was accomplished.

That is, this invention is a separating and measuring process characterized in that a complex (or a labeled complex) dissolved in a solution is separated from free affinity substance (or analyte to be measured) by use of a membrane having specific separating capability.

The separating and measuring process of this invention is practised, for example, as shown in FIG. 6, as follows.

When the separating and measuring process of this invention on the principle of so-called non-competitive reaction is practised, a sample containing an analyte to be measured is first reacted with a labeled or unlabeled affinity substance, if necessary, by their addition to and mixing in a suitable buffer solution, to form a complex. The complex is then separated from free affinity substance by use of a membrane having a suitable specific separating capability. Subsequently, the amount of the labeling substance or the affinity substance which is contained in the complex separated is determined by a measuring method suitable for properties of the labeling substance or the affinity substance. Separately, measurement is carried out in the same manner as above by using a sample containing a known concentration of the analyte, and there is prepared a calibration curve showing the relationship between the amount of the analyte and the amount of the labeling substance or the affinity substance in the complex. The amount of the analyte corresponding to the amount of the labeling substance or the affinity substance in the complex is determined using the calibration curve, whereby the amount of analyte in the sample can be measured.

Figure 7:
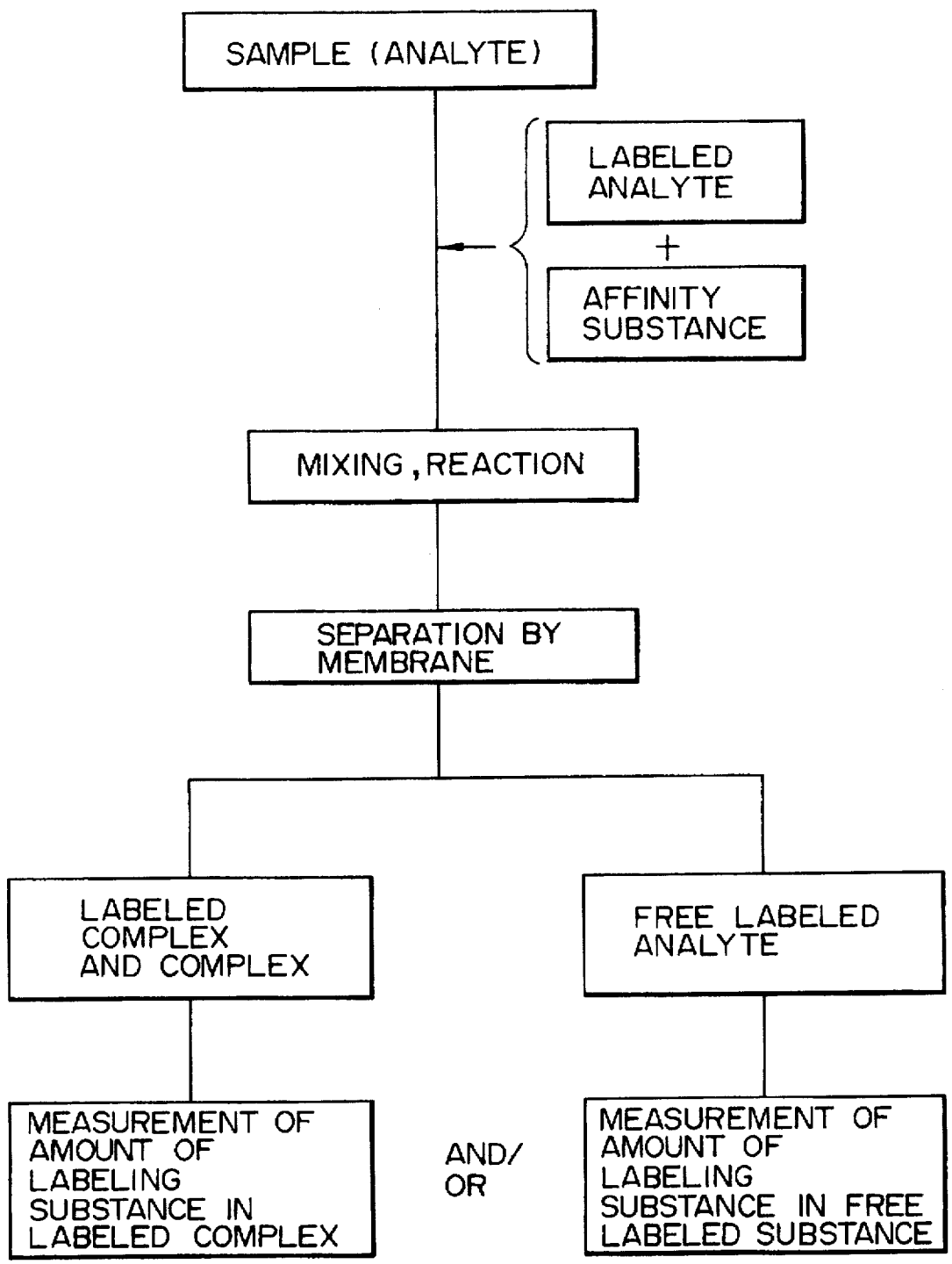

The separating and measuring process of this invention on the principle of so-called competitive reaction can be practised, for example, as shown in FIG. 7, as follows.

A sample containing an analyte to be measured, labeled analyte and an affinity substance are first reacted, if necessary, by their addition to and mixing in a suitable buffer solution, to form a complex and a labeled complex. The labeled complex is then separated from free labeled analyte by use of a membrane having a suitable specific separating capability. Subsequently, the amount of the labeling substance contained in the labeled complex thus separated is determined by a measuring method suitable for properties of the labeling substance. Separately, measurement is carried out in the same manner as above by using a sample containing a known concentration of the analyte to be measured, and there is prepared a calibration curve showing the relationship between the amount of the analyte and the amount of labeling substance in the labeled complex. The amount of the analyte corresponding to the amount of labeling substance in the labeled complex is determined using the calibration curve, whereby the amount of analyte in the sample can be measured.

An analyte which can be measured by the measuring process of this invention is not critical so long as it satisfies the following condition i) or ii). i) There exists an affinity substance which can form a complex with the analyte by the interaction (affinity) between the affinity substance and the analyte, and said affinity substance can be measured (detected) in itself by some method or can be labeled with some labeling substance. ii) The analyte itself can be labeled with some labeling substance, and there exists an affinity substance which can form a labeled complex with the analyte by the interaction between the affinity substance and the analyte. Typical examples of the analyte are proteins, peptides, nucleic acids, saccharides, lipids, hormones and drugs which are contained in samples derived from living bodies, for example, body fluids such as serum, blood, plasma, urine and the like, lymphocytes, hemocytes, and various cells: and synthetic substances such as synthetic saccharides, synthetic peptides, synthetic nucleic acids, etc. More specific examples of the analyte are tumor markers such as α-fetoprotein (AFP), CA19-9, prostate gland specific antigen (PSA), carcinoembryonic antigen (CEA), substances having special sugar chains which cancerous cells produce, and the like; serum proteins such as immunoglobulin A (IgA), immunoglobulin E (IgE), immunoglobulin G (IgG), $β_2$-microglobulin, albumin, ferritin, and the like; peptides such as C-peptide, angiotensin I, and the like; enzyme proteins such as amylase, alkaline phosphatases, γ-glutamyl transpeptidase (γ-GTP), and the like; antiviral antibodies against clinically noted viruses such as rubella virus, herpesvirus, hepatitis virus, ATL virus, AIDS virus and the like; deoxyribonucleic acid (DNA) and ribonucleic acid (RNA) of pathogens such as viruses and the like, or single-stranded polynucleotides constituting nucleic acids; antigenic substances derived from pathogens such as viruses and the like; antibodies reactive with allergens such as pollen of trees and plants, such as cryptomeria, indoor dust and the like; saccharides such as water-soluble polysaccharides, oligosaccharides, monosaccharides, etc. which are derived from natural polysaccharides [specific examples of the saccharides are glycoproteins (e.g. AFP, human chorionic gonadotropin (hCG), transferrin and IgG); gangliosides (e.g. GM1, GM2 and GD2); ceramides of globo type, lacto type and the like; polysaccharides and oligosaccharides, which are derived from glycoproteins, gangliosides, ceramides, etc.; and natural polysaccharides (e.g. starch, cellulose and chitin) or oligosaccharides derived therefrom]; lipids such as lipoproteins and the like; proteases such as trypsin, plasmin, serine protease, and the like; hormones such as insulin, hCG, thyroxine (T4), triiodothyroxine (T3), prolactin, thyroid stimulating hormone (TSH), and the like; and drugs such as digoxin, phenytoin, morphine, nicotine, and the like.

The substance having affinity for the analyte which is used in this invention is not critical so long as it forms a complex with the analyte by the interaction between the affinity substance and the analyte and if necessary, the affinity substance can be measured (detected) in itself by some method or can be labeled with some measurable (detectable) labeling substance (this does not apply to the case where the analyte itself can be labeled with some labeling substance). The affinity substance includes antibodies against substances having antigenicity (including haptens); antigens against antibodies; lectins having affinity for sugar chains having a specific structure, such as concanavalin A, Lens culinaris lectin, Phaseolus vulgaris lectin, Datura stramonium lectin, Triticum vulgaris lectin, and the like; inhibitors for specific enzymes, such as $α_1$-anti-trypsin for trypsin, $α_2$-macroglobulin for plasmin, $α_2$-macroglobulin for serine protease, and the like; and polynucleotide chains complementary to single-stranded polynucleotides which are analytes to be measured.

As the present inventive affinity substance which itself can be measured (detected) by some method, there can be exemplified substances which themselves have properties as labeling substances, such as enzymes, substances which can emit fluorescence, luminescent substances, substances which can absorb an ultraviolet light, and the like.

More specific examples of combinations of the above analytes and affinity substances are as shown in Table 1.

TABLE 1

| Analyte | Affinity substance |
| --- | --- |
| Substance having antigenecity (including haptens) | Antibodies |
| Saccharides (sugar chains) | Lectins |
| Inhibitors | Proteases |
| Proteases | Inhibitors |
| Antibodies | Antigen against antibodies as analytes |
| Nucleic acids | Complementary polynucleotides |
| Lectins | Saccharides (sugar chains) |

The labeling substance according to this invention includes, for example, enzymes such as alkaline phosphatases, β-galactosidase, peroxidase, microperoxidase, glucose oxidase, glucose-6-phosphate dehydrogenase, malate dehydrogenase, luciferase, etc., which are used, for example, in EIA; radioisotopes such as $^{99m}$Tc, $^{131}$I, $^{125}$I, $^{14}$C, $^3$H, etc., which are used, for example, in RIA; substances which can emit fluorescence, such as fluorescein, dansyl residue, fluorescamine, coumarin, naphthylamine, derivatives thereof, etc., which are used, for example, in FIA; luminescent substances such as luciferin, isoluminol, luminol, bis(2,4,6-trifluorophenyl) oxalate, etc.; substances which can absorb an ultraviolet light, such as phenol, naphthol, antracene, derivatives thereof, etc.; and substances having properties as spin, which are represented by compounds having an oxyl group, such as 4-amino-2,2, 6,6-tetramethylpiperidin-1-oxyl, 3-amino-2,2,5,5-tetramethylpyrrolidin-1-oxyl, 2,6-di-t-butyl-α-(3,5-di-t-butyl-4-oxo-2,5-cyclohexadien-1-ylidene)-p-tolyloxy, etc. Needless to say, the labeling substances are not limited to these substances.

As a method for attaching the above-mentioned labeling substance to the affinity substance or the analyte to be measured, there can be exemplified all of conventional labeling methods which are generally employed, for example, in conventional EIA, RIA and FIA (e.g. Yuichi Yamamura "Ikagaku Jikken Koza Vol. 8" 1st ed., NAKAYAMA-SHOTEN Ltd., 1971; Akira Kawano "Zusetsu Keiko-kotai" 1st ed., Soft Science, Inc., 1983; and Eiji Ishikawa, Tadashi Kawai and Kiyoshi Miyai "Koso Men-eki Sokuteiho", 2nd ed., IGAKU-SHOIN Ltd.). The attachment may be carried out according to these methods. Needless to say, the attachement may be carried out by a conventional method utilizing the reaction of avidin (or streptoavidin) with biotin.

In the separating and measuring process of this invention, the reaction conditions for reacting the analyte to be measured with the labeled or unlabeled affinity substance to form a complex, or the reaction conditions for reacting the analyte to be measured with the labeled analyte and the affinity substance to form a labeled complex, are not critical so long as the reaction conditions do not inhibit the formation of the complex (or the labeled complex). The reaction may be carried out under reaction conditions employed for forming a complex in a conventional method, for example, EIA, RIA, FIA or affinity chromatography. For example, when a buffer solution is used in the reaction, as the buffer and other reagents, those used in the above conventional methods may be properly chosen.

In the separating and measuring process of this invention which utilizes the noncompetitive reaction principle, although the concentration of the affinity substance used for forming a complex is varied depending on a value at which the limit of measurement of the analyte is set, it is usually preferable that the affinity substance is present in the reaction solution at a concentration which is not less than (preferably 2 times or more as high as, more preferably 5 times or more as high as) a concentration at which the affinity substance can bind to the whole of the analyte of a concentration corresponding to the limit of measurement.

In the separating and measuring process of this invention which utilizes the competitive reaction principle, the concentrations of the affinity substance and the labeled analyte used for forming a labeled complex are not critical and may be properly determined depending on values at which the limit of measurement of the analyte and the measurement sensitivity are set, respectively. However, needless to say, the using concentration of the labeled analyte should be not less than a concentration at which the labeled analyte can bind to the whole affinity substance present in the reaction solution.

In the separating and measuring processes of this invention, although the pH at the reaction is not critical so long as it does not inhibit the formation of the complex (or the labeled complex), it is usually 2 to 10, preferably 5 to 9. Although the temperature at the reaction is also not critical so long as it does not inhibit the formation of the complex for the labeled complex), it is usually 0° to 50° C., preferably 20° to 40° C. As to the reaction time, since the time required for the formation of the complex (or the labeled complex) varies depending on properties of the analyte to be measured and the affinity substance, the reaction may be properly carried out for several seconds to several hours, depending on their properties.

In the separating and measuring processes of this invention, the membrane having specific separating capability which is used for the B/F separation is not critical so long as it permits separation of the complex (or the labeled complex) from the free affinity substance (or the free labeled analyte) by means of the difference in properties between them. The membrane having specific separating capability is properly selected from various membranes, depending on the difference in properties between the complex (or the labeled complex) and the free affinity substance (or the free labeled analyte). Individual membranes are explained below.

When the molecular weight of the complex (or the labeled complex) is about 1.2 times or more, preferably 1.5 times or more, the molecular weight of the affinity substance (or the labeled analyte), an ultrafiltration membrane is suitable. The ultrafiltration membrane is not critical so long as it is one which is used in usual ultrafiltration. Preferable examples of the ultrafiltration membrane are membranes made of cellulose acetate, nitrocellulose, mixed ester of cellulose acetate and nitrocellulose, regenerated cellulose, polyvinyl chloride, polytetrafluoroethylene, acrylic acid copolymer, polyamide, polysulfone or TEFLON® (synthetic resin polymers and products). As such ultrafiltration membranes, those having a cut-off molecular weight of 10,000, 30,000, 50,000, 100,000, etc. are now on the market. These membranes can be used, for example, for separating a complex (or a labeled complex) obtained by using any of the combinations of an analyte and an affinity substance shown in Table 1, from free affinity substance (or free labeled analyte).

When the difference between the isoelectric point of the complex (or the labeled complex) and that of the affinity substance (or the labeled analyte) is 0.1 or more, preferably 0.3 or more, an ion-exchange membrane is suitable. Ion-exchange membranes are membranes having one or more charged groups attached as ion-exchange groups to constituents of membrane and are classified into cation-exchange membranes, anion-exchange membranes and amphoteric ion-exchange membranes, according to the kind of the ion-exchange groups. The cation-exchange membranes having one or more cation-exchange groups are permeable selectively to cations. The cation-exchange groups include sulfonic acid group, phosphoric acid group, phosphonic acid group, sulfate ester groups, phosphoric ester groups, carboxylic acid groups, phenolic hydroxyl group, nitro group, mercapto group, hydroxyl group, acid amide groups, etc. The anion-exchange membranes having one or more anion-exchange groups are permeable selectively to anions. The anion-exchange groups include ammonium group, sulfonium group, phosphonium group, primary to tertiary amino groups, etc. In the amphoteric ion-exchange membranes having both cation-exchange and anion-exchange groups, their ion-exchange properties vary depending on the dissociation constants of the ion-exchange groups: at a pH higher than a certain pH, cation-exchange properties are predominant, and at a pH lower than the certain pH, anion-exchange properties are predominant. The ion-exchange membrane includes, for example, commercially available ones such as DEAE MemSep, CM MemSep (both mfd. by Japan Millipore Ltd.), Zetaprep (mfd. by Cuno Co.) having ion-exchange groups such as quaternary aminoethyl group (QAE group), diethylaminoethyl group (DEAE group) and sulfopropyl group (SP group), etc. These ion-exchange membranes are properly chosen depending on the difference between the isoelectric points of the complex (or the labeled complex) and the affinity substance (or the labeled analyte) which are to be separated from each other. These membranes can also be used, for example, for separating a complex (or a labeled complex) obtained by using any of the combinations of an analyte and an affinity substance shown in Table 1, from free affinity substance (or free labeled analyte).

When the complex (or the labeled complex) and the affinity substance (or the labeled analyte) are different from each other in hydrophobicity, a hydrophobic membrane is suitable. The hydrophobic membrane has one or more hydrophobic groups such as alkyl groups (e.g. methyl group, ethyl group, propyl group, butyl group, octyl group, octadecyl group, etc.), aromatic groups (e.g. phenyl group, naphthyl group, etc.), etc. which are attached to constituents of membrane, and it is permeable selectively to hydrophobic compounds. Such a hydrophobic membrane can also be used, for example, for separating a complex (or a labeled complex) obtained by using any of the combinations of an analyte and an affinity substance shown in Table 1, from free affinity substance (or free labeled analyte).

In the separating and measuring process of this invention, the B/F separation is carried out by a conventional separating method using a membrane, except for using the above-mentioned membrane having specific separating capability. A specific example of the conventional method is filtration by centrifugation, pressurizing, suction, etc. In the case of centrifugation, it is preferable to use, in particular, a filter-attached tube for centrifuge (e.g. Japanese Patent Unexamined Publication No. 62-176560).

In the measuring processes of this invention, the labeling substance or the affinity substance which is contained in the complex (or the labeled complex) separated by the membrane having specific separating capability is measured by a predetermined method, depending on the kind of the labeling substance or the affinity substance. For example, when the labeling substance or the affinity substance is an enzyme, the measurement is carried out according to a conventional method of EIA, for example, the method described in Tsunehiro Kitagawa, Toshio Nanbara, Akio Tsuji, and Eiji Ishikawa "Koso Men-eki Sokuteiho", an extra issue No. 31 of Tanpakushitsu Kakusan Koso, pp. 51-63, KYORITSU-SHUPPAN Ltd., published on Sep. 10, 1987, etc. For example, when an enzyme-labeled complex remains on the membrane, a procedure after the separation can be simplified by adding a substrate for the labeling enzyme to the membrane after the separation and reacting the same as it is. When the labeling substance is a radioisotope, the measurement is carried out according to a conventional method of RIA by properly choosing and using a measuring instrument such as GM counter, liquid scintillation counter, well-type counter, or the like, depending on the kind and intensity of a radiation emitted by said radioactive substance (see, for example, Yuichi Yamamura "Ikagaku Jikken Koza Vol. 8" 1st ed., NAKAYAMA-SHOTEN Ltd. 1971). When the labeling substance or the affinity substance is a substance which can emit fluorescence, the measurement is carried out according to a conventional method of FIA using a measuring instrument such as fluorometer, for example, the method described in Akira Kawano "Zusetsu Keikokotai" 1st ed., Soft Science, Inc., 1983, etc. When the labeling substance or the affinity substance is a luminescent substance, the measurement is carried out according to a conventional method using a measuring instrument such as photon counter, for example, the method described in Tsunehiro Kitagawa, Toshio Nanbara, Akio Tsuji and Eiji Ishikawa "Koso Men-eki Sokuteiho", an extra issue No. 31 of Tanpakushitsu Kakusan Koso, pp. 252-263, KYORITSU-SHUPPAN Ltd., published on Sep. 10, 1987, etc. When the labeling substance or the affinity substance is a substance which can absorb an ultraviolet light, the measurement is carried out by a conventional method using a measuring instrument such as spectrophotometer. When the labeling substance is a substance having properties as spin, the measuring is carried out according to a conventional method using an electron spin resonance apparatus, for example, the method described in Tsunehiro Kitagawa, Toshio Nanbara, Akio Tsuji and Eiji Ishikawa "Koso Men-eki Sokuteiho" an extra issue No. 31 of Tanpakushitsu Kakusan Koso, pp. 264-271, KYORITSU-SHUPPAN Ltd., published on Sep. 10, 1987, etc.

Needless to say, the labeling substance or the affinity substance may be measured by use of, for example, a reagent for measuring the labeling substance or the affinity substance, respectively, in clinical examination, or by a generally known method for measuring the labeling substance or the affinity substance, respectively. A specific example of such a case is as follows.

When human chorionic gonadotropins (hCG) different in sugar chain structure derived from choriocarcinoma cells are separated and measured, a sample containing these hCG species is reacted, for example, with *Datura stramonium* lectin, after which the separation is carried out by the process of this invention, and hCG in a filtrate or a supernatant is measured using a commercially available reagent for EIA, whereby there can be determined the amount of hCG reactive or unreactive with *Datura stramonium* lectin which is contained in the sample.

In the present inventive separating and measuring process on the noncompetitive reaction principle, when an antibody is used as the affinity substance, the antibody may be used after being properly digested with an enzyme such as pepsin or papain into F(ab')$_2$, Fab' or Fab, depending on purposes. In the case of using a monoclonal antibody having a property of binding only to one epitope site, when a product obtained by attaching a labeling substance to Fab' or Fab obtained by digesting the monoclonal antibody is used as the affinity substance, the labeling substance can be bound to the analyte to be measured, in a proportion of 1 molecule per molecule of the analyte (or in a proportion of 1 molecule per molecule of monomer in the case where the analyte is a dimer, a trimer or the like), and hence property such as molecular weight, isoelectric point and the like of the complex becomes constant, so that the quantitativeness at the time of measurement is improved. Therefore, the employment of said product is preferable.

Also in the separating and measuring process on the competitive reaction principle, when an antibody is used as the affinity substance, the antibody may be used after being properly digested with an ezyme such as pepsin or papain into F(ab')$_2$, Fab' or Fab, depending on purposes. Particularly in the case of using a monoclonal antibody having a property of binding only to one epitope site, when Fab' or Fab obtained by digesting the monoclonal antibody is used as the affinity substance, the affinity substance can be bound to the unlabeled analyte or the labeled analyte in a proportion of 1 molecule per molecule each of the unlabeled analyte or the labeled analyte (or in a proportion of 1 molecule per molecule of monomer in the case where the analyte to be measured is a dimer, a trimer or the like), and hence properties such as molecular weight, isoelectric point and the like of the labeled complex become constant, so that the separation becomes easy. Therefore, the employment of Fab' or Fab is preferable.

Needless to say, in the measuring process of this invention, the amount of analyte can be measured not only by measuring the amount of the labeling substance or the affinity substance in the complex (or the labeling substance in the labeled complex) formed by the interaction; but also by measuring the amount of the labeling substance in free labeled affinity substance which has not participated in the formation of the complex, or the amount of free affinity substance, or by measuring the amount of the labeling substance in free labeled analyte.

As the antibody used as affinity substance in this invention, there may be used either polyclonal antibodies prepared by immunizing animals such as horse, cattle, sheep, rabbit, goat, rat, mouse, etc. with an analyte to be measured, according to a conventional method, for example, the method described in Tadashi Matsuhashi et al. "Menekigaku Jikken Nyumon" 2nd. ed., GAKKAI-SHUPPAN CENTER Ltd., 1981, etc., or monoclonal anitobidies produced by Hybridomas obtained by fusing cells from a tumor line of mouse together with mouse spleen cells previously immunized with an analyte to be measured, according to the conventional method, i.e., the cell fusion method established by G. Köhler and C. Milstein (Nature, 256, 495, 1975). These polyclonal and/or monoclonal antibodies may be used singly or in proper combination of two or more thereof.

In the separating and measuring processes of this invention, for forming the complex (or the labeled complex), there are, if necessary, employed two or more affinity substances (specifically, two or more affinity substances which bind to different sites, respectively, on the analyte to be measured). This employment results in a higher molecular weight of the complex (or the labeled complex) and variation of its isoelectric point. Therefore, the separation of the complex (or the labeled complex) from free affinity substances (or free labeled analyte) becomes more easy, so that the precision of measurement can be improved. Furthermore, the measurement sensitivity, of course, can be increased by attaching a labeling substance to each affinity substance.

In the measuring process on the noncompetitive reaction principle, the measurement sensitivity may be controlled by combined use of labeled affinity substance and unlabeled one. When the reaction is carried out by the combined use of them, the analyte to be measured reacts with both the labeled affinity substance and the unlabeled one to form a comlex containing the labeling substance and a complex containing no labeling substance. The ratio of the former complex to the latter complex is proportional to the ratio of the labeled affinity substance to the unlabeled one at the time of reaction. Therefore, the measurement sensitivity can be controlled when the proportion of the complex containing the labeling substance is varied by varying the proportion of the unlabeled affinity substance, and the analyte to be measured is measured by determining the amount of the labeling substance in the complex. In this case, although the labeled affinity substance and the unlabeled affinity substance are usually derived from the same affinity substance, they may, of course, be different in the kind of affinity substance so long as they are such that when one of them binds to the analyte to be measured, the other cannot bind thereto.

When the interaction between an analyte to be measured and an affinity substance is weak, so that a complex which is formed from them and dissolved in a solution, tends to be dissociated into the analyte and the affinity substance, or when the binding strength of an analyte to be measured to an affinity substance is seemingly weak because the concentration of the analyte is low, the process of this invention are particularly effective in separating the complex from free affinity substance (or free labeled analyte) and measuring the analyte. In detail, when the complex formed by a weak binding strength is separated from the free affinity substance (or the free labeled analyte) using a high pressure liquid chromatography and the analyte is measured, the complex and the free affinity substance (or the free labeled analyte) are diluted with the progress of the separation in a column, resulting in a change of the equilibrium state. Therefore, the complex is dissociated into the analyte and the affinity substance, so that the separation and measurement of the analyte become inaccurate. Such a phenomenon tends to occur particularly when the separation and measurement are carried out by combination of a saccharide and a lectin. When the process of this invention is employed in such a case, the complex can be separated from the free affinity substance (or the free labeled analyte) without dissociating the complex into the analyte and the affinity substance, so that the analyte can be accurately separated and measured.

The process of this invention permits not only easy and efficient separation and measurement of trace components in samples derived from living bodies, synthetic saccharides, substances having specific affinity, etc., but also measurement of the interaction (or affinity) activity of substances having specific affinity.

Furthermore, the separating process of this invention is effective also as a pretreatment process in the measuring process in which the B/F separation is carried out by a high pressure liquid chromatography (HPLC) and which has been disclosed in Japanese Patent Unexamined Publication No. 2-28557. For example, when a high concentration of an affinity substance is used in the above process using HPLC, the separating capability in the B/F separation is lowered because the concentration of free affinity substance is higher than that of the complex. On the other hand, the process using the membrane permits the separation even when a relatively high concentration of an affinity substance is used. Therefore, when the B/F separation by HPLC is carried out after removing free affinity substance to a certain extent previously by use of the membrane having specific separating capability which is used in the measuring process of this invention, a satisfactory separation result can be obtained, so that a satisfactory measurement result can be obtained even when a high concentration of affinity substance is used.

The process of this invention makes it possible to separate and measure trace components more easily in a shorter time with much higher precision, as compared with solid phase method, double antibody technique, methods using affinity chromatography, etc. which have been employed in conventional EIA, RIA or FIA. For example, in the case where the combination of an analyte to be measured and an affinity substance is a combination of antigen and antibody, when the analyte is measured by a conventional method, at least, several hours, in some cases, several days, are required for obtaining a measurement result. According to the process of this invention, the time required for the measurement is usually as very short as several tens of minutes.

In the process of this invention, the reaction of the analyte to be measured with the affinity substance proceeds in a liquid phase and hence is a homogeneous reaction. Therefore, the process is advantageous, for example, in that the reaction time is short and that the reproducibility of measurement result is high.

Moreover, the process of this invention is effective in that it permits dealing with a large number of samples at the same time in a short time and merely requires a simpler procedure, as compared with the measuring process in which the B/F separation is carried out by HPLC.

This invention is more concretely explained below with reference to Examples, which are not by way of limitation but by way of illustration.

REFERENTIAL EXAMPLE

[Labeled Oligosaccharide Solution]

Oligosaccharide chains were prepared from human transferrin (available from Sigma Chemical Co.) by the hydrazinolysis method and labeled with fluorescence by use of 2-aminopyridine by a conventional method. Then, the labeled oligosaccharides thus obtained were treated by a reverse phase column chromatography, and only a bianntennary complex type oligosaccharide chain labeled with fluorescence by 2-aminopyridine was separated and then dissolved in water to a concentration of 1 nmol/µl to obtain a labeled oligosaccharide solution.

[Lectin Solution]

A lectin solution was prepared by dissolving concanavalin A (available from Honen Corporation) in 10 mM tris (hydroxyemthyl)aminomethane (Tris)-hydrochloric acid buffer (pH 7.4, containing 100 mM sodium chloride, 1 mM manganese chloride, 1 mM calcium chloride and 1 mM magnesium chloride) to a concentration of 100 µg/ml.

[Procedure]

With 1 µl of the labeled oligosaccharide solution was mixed 100 µl of the lectin solution with ice-cooling, and the reaction was carried out for 20 minutes. A portion of the reaction solution was centrifuged at 12,000 r.p.m. and 4° C. for 20 minutes by use of a tube for centrifugal filtration (Ultrafree C3LGC, cut-off molecular weight 10,000, mfd. by Japan Millipore Ltd.) to obtain a filtrate.

As samples, 10 µl each of the reaction solution and the filtrate were analyzed by a high pressure liquid chromatography [column: Wakopak 5C18 (mfd. by Wako Pure Chemical Industries, Ltd.), eluent: 0.1M ammonium acetate buffer (pH 4.0), 0.5 to 5% methanol concentration gradient, detection: a fluorescence detector (excitation wavelength 320 nm, emission wavelength 400 nm)], and the peak height of the labeled oligosaccharide was measured for each sample.

For comparison, analysis by centrifugal filtration and high pressure liquid chromatography was carried out under the same conditions as above also for a solution obtained by mixing 1 µl of the labeled oligosaccharide solution with 100 µl of 10 mM Tris-hydrochloric acid buffer (pH 7.4, containing 100 mM sodium chloride, 1 mM manganese chloride, 1 mM calcium chloride and 1 mM magnesium chloride) (hereinafter the solution thus obtained is abbreviated as "standard sample"), and the peak height of the labeled oligosaccharide was measured for each of the standard sample and a filtrate obtained by centrifugal filtration of the standard sample (hereinafter the filtrate is abbreviated as "standard filtrate").

[Results]

The results obtained are shown in Table 2.

TABLE 2

| Sample | Peak height (µV) |
| --- | --- |
| Reaction solution | 8702 |
| Filtrate | 3874 |
| Standard sample | 8746 |
| Standard filtrate | 8688 |

From the results shown in Table 2, it can be seen that the peak height of the filtrate is about 45% of that of the standard filtrate and that the peak heights of the reaction solution and the standard filtrate are substantially the same as that of the standard sample. These facts are judged to indicate that a lectin-labeled oligosaccharide complex formed in the reaction solution is completely dissociated during the analysis by the high pressure liquid chromatography.

From the results described above, it can be seen that it is difficult to separate a saccharide-lectin complex from free saccharide by using a high pressure liquid chromatography.

EXAMPLE 1

Measurement of Human Chorionic Gonadotropin (hCG)

[Antibody Solution 1]

Anti-hCG-α chain monoclonal antibody obtained by culturing a mouse hybridoma clone producing anti-hCG-α chain antibody which had been prepared by a conventional method, was made into Fab' by a conventional method. This Fab' was labeled with horseradish peroxidase (POD) by a conventional method, and thus obtained POD-labeled hCG-α chain-Fab' was added to 50 mM phosphate buffer [pH 7.5, containing 150 mM sodium chloride and 0.2% bovine serum albumin (available from Sigma Chemical Co.) to adjust the protein concentration to 50 µg/liter, whereby antibody solution 1 was obtained.

[Antibody solution 2]

Antibody solution 2 was prepared by adding anti-hCG-β chain (mouse) monoclonal antibody (available from Wako Pure Chemical Industries, Ltd.) to 50 mM phosphate buffer (pH 7.5, containing 150 mM sodium chloride) to adjust the protein concentration to 5 mg/liter.

[Samples]

Solutions having a hCG concentration of 0, 100, 200, 300 or 400 mIU/ml were prepared as samples by dissolving commercially available hCG (available from Sigma Chemical Co.) in 50 mM phosphate buffer [pH 7.5, containing 150 mM sodium chloride and 0.2% bovine serum albumin (available from Sigma Chemical Co.)].

[Substrate Solution 1]

Substrate solution 1 was prepared by dissolving 1.66 g of 3-(p-hydroxyphenyl)-propionic acid in 1,000 ml of 50 mM phosphate buffer (pH 7.5, containing 150 mM sodium chloride), and adjusting the resulting solution to pH 7.5 with 6N sodium hydroxide.

[Substrate solution 2]

A 20 mM hydrogen peroxide solution was prepared as substrate solution 2 by diluting a 35% aqueous hydrogen peroxide solution with phosphate buffer (pH 7.5, containing 150 mM sodium chloride).

[Measuring Procedure]

At room temperature, 80 µl of antibody solution 1, 80 µl g of antibody solution 2 and 20 µl of each sample were mixed, and the reaction was carried out for 1 hour. Then, the reaction mixture was subjected to centrifugal filtration at 3,000 r.p.m. for 10 minutes by use of a tube for centrifugal filtration [Ultrafree CL (cut-off molecular weight: 100,000), mfd. by Japan Millipore Ltd.]. To 10 µl of the filtrate were added 900 µl of substrate solution 1 and 100 µl of substrate solution 2, and the POD activity in the filtrate was measured in terms of an increase of the intensity of fluorescence per minute at an excitation wavelength of 320 nm and an emission wavelength of 404 nm.

[Results]

Figure 1:
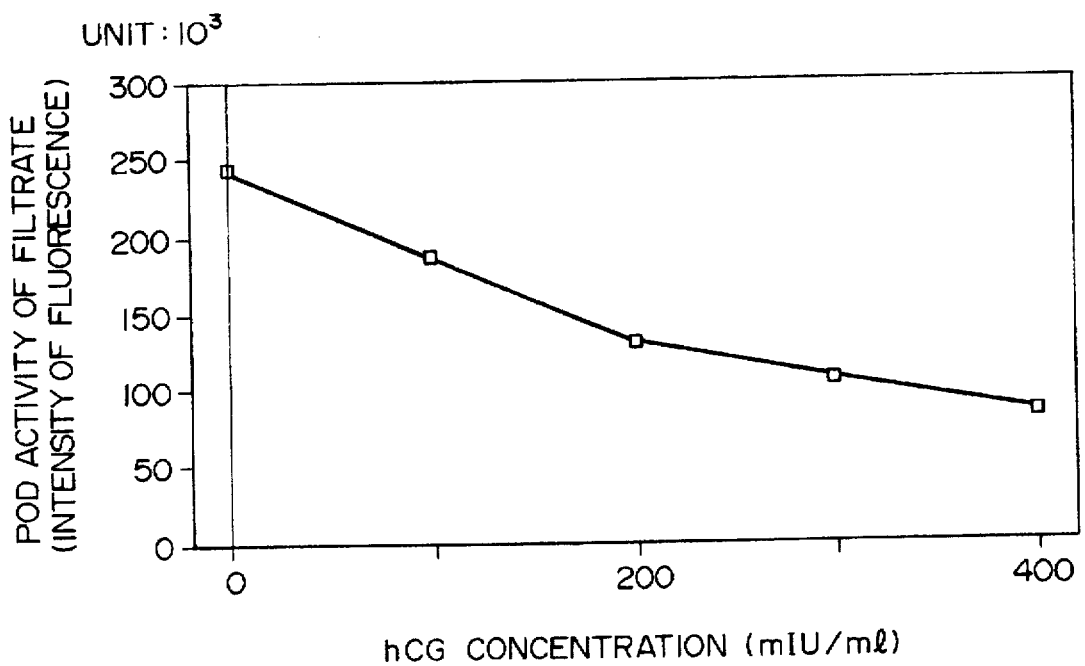
FIG. 1 shows a calibration curve for hCG concentration which was obtained in Example 1.

FIG. 1 shows a calibration curve showing the relationship between the hCG concentration of the sample and the POD activity of the filtrate (the intensity of fluorescence). As is clear from FIG. 1, the calibration curve showed good linearity.

EXAMPLE 2

Measurement of the Change of Sugar Chain of the Human Chorionic Gonadotropin (hCG) of a Patient with Choriocarcinoma

[Lectin Solution]

A lectin solution was prepared by purifying *Datra stramonium* lectin (Datura lectin) from seeds of Jimsonweed by the method of Goldstein I. J. et al., and adding the same to 50 mM phosphate buffer [pH 7.5, containing 150 mM sodium chloride and 0.2% bovine serum albumin (available from Sigma Chemical Co.)] to adjust the protein concentration to 1 mg/ml.

[Sample 1]

hCG extracted from the urine of a patient with choriocarcinoma by Permutit method (J.C.B., 148, 501, 1943) was purified by various chromatographics and added to 50 mM phosphate buffer [pH 7.5, containing 150 mM sodium chloride and 0.2% bovine serum albumin (available from Sigma Chemical Co.)] to adjust the protein concentration to 50 ng/ml, whereby sample 1 was obtained.

[Sample 2]

Sample 2 was prepared by dissolving hCG (available from Sigma Chemical Co.) of a normal pregnant woman in 50 mM phosphate buffer pH 7.5, containing 150 mM sodium chloride and 0.2% bovine serum albumin (avaialble from Sigma Chemical Co.)] to adjust the protein concentration to 50 ng/ml.

[Measuring Procedure]

With 50 µl of the lectin solution was mixed 50 µl of each sample at room temperature and the reaction was carried out for 30 minutes. Then, the reaction mixture was subjected to centrifugal filtration at 3,000 r.p.m. for 20 minutes by use of a tube for centrifugal filtration [Ultrafree CL (cut-off molecular weight: 100,000) mfd. by Japan Millipore Ltd.]. The hCG concentration of the filtrate was measured by the method described in Example 1.

[Results]

The hCG concentration of the filtrate is shown for each sample in Table 3. As is clear from Table 3, the changed sugar chain portion of hCG of the patient with choriocarcinoma and Datura lectin bound to each other and did not pass through the filter, so that the hCG concentration of the filtrate was decreased. This result reveals that the sugar chain of 85% of the whole hCG of the patient with choriocarcinoma had been changed with canceration.

TABLE 3

|  | Sample 1 | Sample 2 |
|---|---|---|
| hCG concentration of filtrate | 7.5 ng/ml | 50 ng/ml |

EXAMPLE 3

Measurement of Hepatitis B-type Virus DNA (HBV-DNA)

[Probe Solution]

By means of a DNA synthesizing machine (Biosearch Inc.), there was synthesized an oligonucleotide (22 mer) having the sequence described below which was specific for a part of the surface antigen gene of hepatitis B-type virus. The oligonucleotide was labeled at the 5'-terminal with horseradish peroxidase (POD) through a bifunctional crosslinking agent. The probe thus obtained was added to 10 mM Tris-hydrochloric acid buffer (pH 8.0) containing 0.15M sodium chloride, to adjust its concentration to 5 µM, whereby a probe solution was obtained.

The sequence of the oligonucleotide:

TGGCCAAAATTCGCAGTCCCCA

[Samples]

A single-stranded M13-HBV-DNA obtained by inserting hepatitis B-type virus genome (about 3 kb) in M13 phage DNA (about 7 kb) was dissolved in water to a concentration of 0, 80, 200 or 400 ng/ml, and the solutions thus prepared were used as samples.

[Substrate Solution 1]

Substrate solution 1 was prepared by dissolving 1.66 g of 3-(p-hydroxyphenyl)-propionic acid in 1,000 ml of 50 mM phosphate buffer (pH 7.5, containing 150 mM sodium chloride), and adjusting the resulting solution to pH 7.5 with 2N sodium hydroxide.

[Substrate Solution 2]

A 20 mM aqueous hydrogen peroxide solution was prepared as substrate solution 2 by diluting a 35% aqueous hydrogen peroxide solution with phosphate buffer (pH 7.5, containing 150 mM sodium chloride).

[Measuring Procedure]

To 10 µl of each sample was added 10 µl of a 0.5M sodium hydroxide solution, and the resulting mixture was allowed to stand at room temperature for 10 minutes, and then neutralized with 10 µl of a 1M Tris-hydrochloric acid solution. With the neutralized mixture were mixed 10 µl of the probe solution, 10 µl of 2% bovine serum albumin (nuclease-free, available from Wako Pure Chemical Industries, Ltd.) and 50 µl of a 5M ammonium acetate solution. The reaction was carried out at room temperature for 1 hour, after which 500 µl of a 2.5M ammonium acetate solution was added to the reaction mixture, and the resulting mixture was concentrated by centrifugation at 2,500 r.p.m. for 10 minutes by use of a tube for ultrafiltration [Ultrafree CL (cut-off molecular weight: 100,000), mfd. by Japan Millipore Ltd.]. To the solution remaining above the filter was added 500 µl of a 2.5M ammonium acetate solution, and the above concentration by centrifugation was repeated twice more. Finally, the volume of solution on the filter was adjusted to 200 µl with a 2.5M ammonium acetate solution (hereinafter the solution thus obtained is referred to as "final sample fluid").

To 50 μl of the final sample fluid were added 900 μl of substrate solution 1 and 100 μl of substrate solution 2, and the POD activity in the final sample fluid was measured in terms of an increase of the intensity of fluorescence per minute at an excitation wavelength of 320 nm and an emission wavelength of 400 nm.

[Results]

Figure 2:
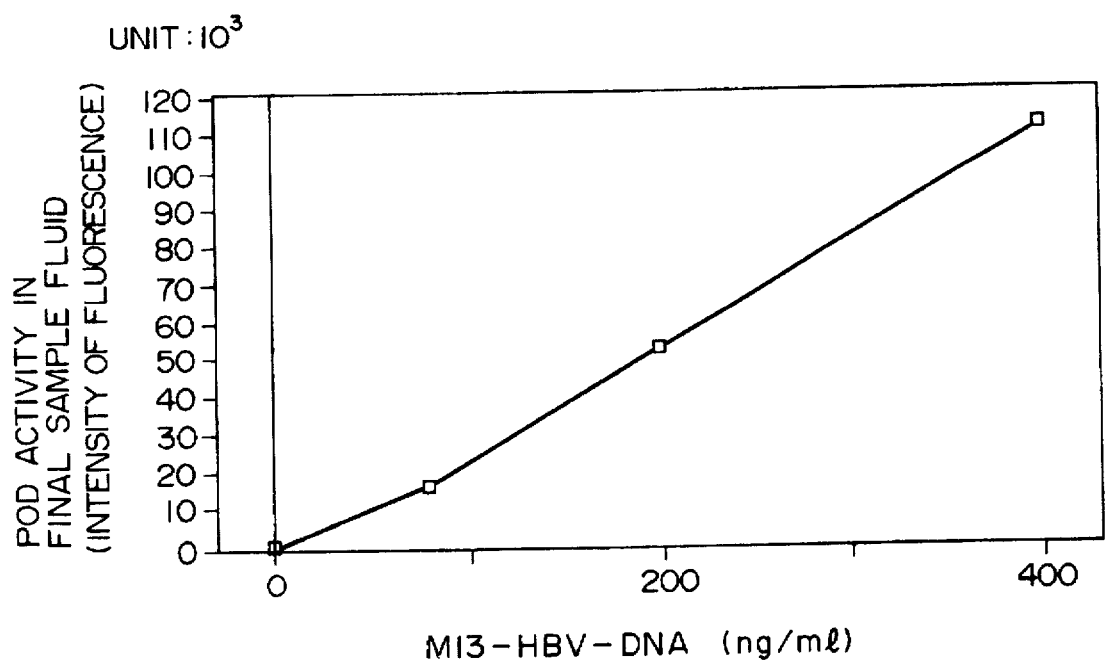
FIG. 2 shows a calibration curve for HBV-DNA concentration which was obtained in Example 3.

FIG. 2 shows the relationship between the HBV-DNA concentration of the sample and the POD activity in the final sample fluid (the intensity of fluorescence). As is clear from FIG. 2, the calibration curve showed good linearity.

EXAMPLE 4

Measurement of a Lectin

[Labeled Oligosaccharide Solution]

Oligosaccharide chains obtained from human transferrin (available from Sigma Chemical Co.) by the hydrazinolysis method were labeled with fluorescence by use of 2-aminopyridine by a conventional method. The labeled oligosaccharide chains were subjected to a reversed phase column chromatography, and only a bianntennary complex type oligosaccharide chain labeled with fluorescence was separated and purified. An aqueous solution of the thus obtained fluorescence-labeled oligosaccharide chain with a concentration of 1 nmol/μl was prepared as a labeled oligosaccharide solution.

[Samples]

Solutions having a concanavalin A (Con A) concentration of 0, 50, 100, 200, 500, 1,000 or 2,000 pmol/ml were prepared as samples by dissolving commercially available Con A (available from Honen Corporation) in 10 mM Tris-hydrochloric acid buffer [pH 7.4, containing 100 mM sodium chloride, 1 mM magnesium chloride, 1 mM calcium chloride, 1 mM manganese chloride and 0.2% bovine serum albumin (available from Sigma Chemical Co.)].

[Measurement Conditions]

With ice-cooling, 1 μl of the labeled oligosaccharide solution and 100 μl of each sample were mixed, and the reaction was carried out for 20 minutes. Then, the reaction mixture was subjected to centrifugal filtration at 12,000 r.p.m. at 4° C. for 20 minutes by use of a tube for centrifugal filtation [Ultrafree C3LGC (cut-off molecular weight: 10,000), mfd. by Japan Millipore Ltd.]. To 50 μl of the filtrate was added 950 μl of water, and the intensity of fluorescence in the resulting mixture was measured at an excitation wavelength of 320 nm and an emission wavelength of 400 nm. The difference between the intensities of fluorescence measured for the sample having a Con A concentration of 0 pmol/ml and each of the other samples was calculated and taken as the amount of bound labeled oligosaccharide.

[Results]

Figure 3:
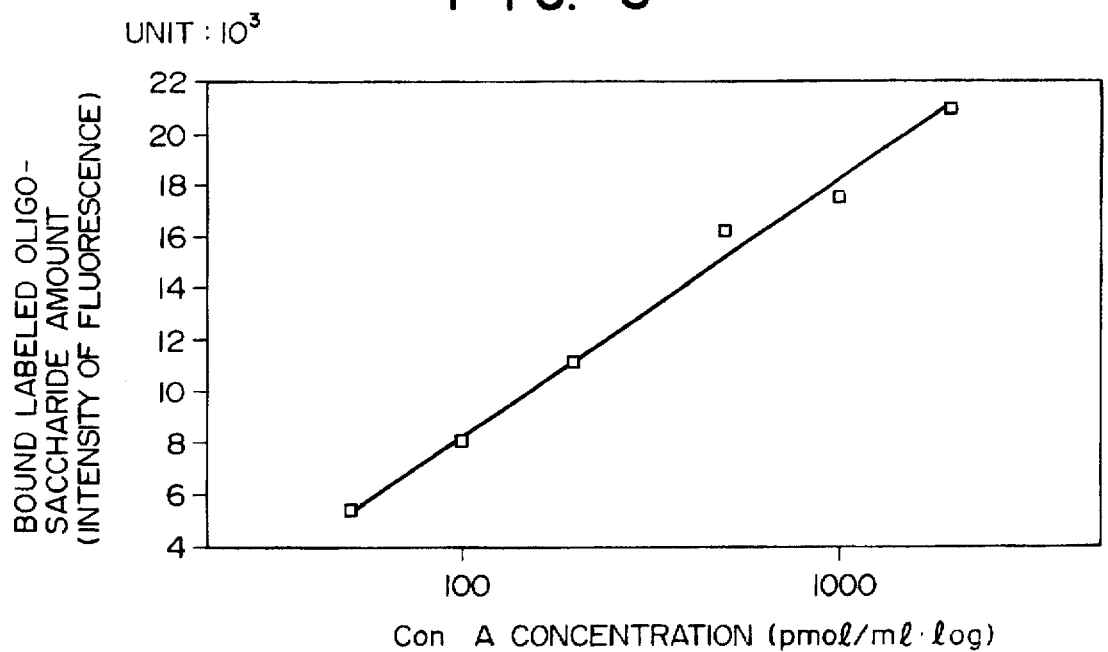
FIG. 3 shows a calibration curve for Con A concentration which was obtained in Example 4.

FIG. 3 shows a calibration curve showing the relationship between the Con A concentration of the sample and the amount of bound labeled oligosaccharide (the intensity of fluorescence). As is clear from FIG. 3, the calibration curve showed good linearity.

EXAMPLE 5

Measurement of the Sugar-chain-structure-recognizing Specificity of a Lectin

[Labeled Oligosaccharides Solution]

Oligosaccharides obtained from bovine fetal serum asialofetuin (available from Sigma Chemical Co.) by the hydrazinolysis method were labeled with fluorescence by use of 2-aminopyridine by a conventional method. An aqueous solution of the labeled oligosaccharides with a concentration of 1 nmol/μl was prepared as a labeled oligosaccharides solution.

[Samples]

Samples were prepared by dissolving each of commercial concanavalin A (Con A, available from Honen Corporation), commercial Ricinus communis lectin (RCA 120, available from Honen Corporation) and Datura lectin (DSA) purified from seeds of Jimsonweed by a conventional method, in 10 mM Tris-hydrochloric acid buffer (pH 7.4, containing 100 mM sodium chloride, 1 mM magnesium chloride, 1 mM calcium chloride and 1 mM manganese chloride) to a concentration of 1 mg/ml.

[Measurement Conditions]

With ice-cooling, 1 μl of the labeled oligosaccharides solution and 100 μl of each sample were mixed, and the reaction was carried out for 20 minutes. Then, the reaction mixture was subjected to centrifugal filtration at 12,000 r.p.m. at 4° C. for 20 minutes by use of a tube for centrifugal filtration [Ultrafree C3LGC (cut-off molecular weight: 10,000), mfd. by Japan Millipore Ltd.]. Thereafter, 10 μl of the filtrate was separated by a high pressure liquid chromatography (reversed phase column chromatography, 0.1M ammonium acetate buffer, pH 4.0, 0–0.25% n-butanol concentration gradient), followed by detection by means of a fluorescense detector (excitation wavelength 320 nm, emission wavelength 400 nm).

[Results]

Figure 4:
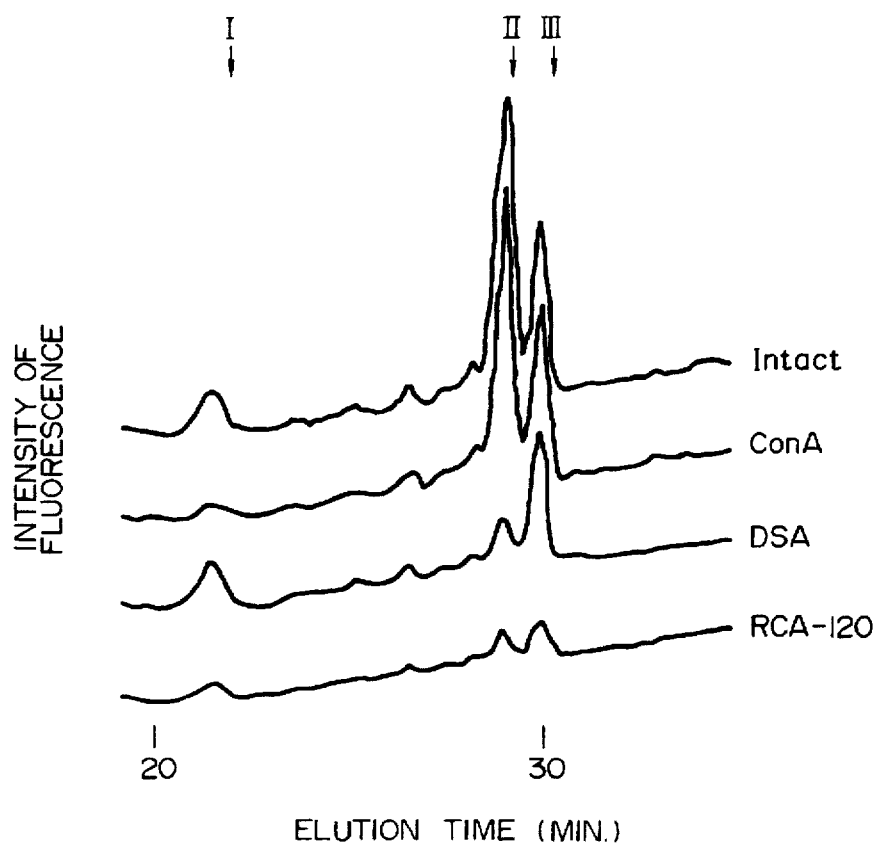
FIG. 4 shows an elution pattern of a sample which was obtained by a high pressure liquid chromatography in Example 5.

FIG. 4 shows elution patterns obtained for the labeled oligosaccharides solution (Intact) and mixtures of each sample and the labeled oligosaccharides solution. Peaks I, II and III are due to the labeled oligosaccharides of the structures shown in FIG. 5. Each lectin caused disappearance of the peak due to the labeled oligosaccharide which had the structure corresponding to the known specificity of the lectin. Thus, the sugar-recognizing specificity of the lectins could be measured.

What is claimed is:

1. A process for measuring the amount of an analyte in a sample which comprises mixing a sample containing an analyte to be measured with an affinity substance having affinity for the analyte labeled with a labeling substance, allowing the analyte to form a complex with the affinity substance, said complex being dissolved in solution and having a molecular weight of about 1.2 times or more as large as that of the affinity substance and having a tendency to be dissociated into the analyte and the affinity substance due to weak interaction, separating the resulting complex of the analyte and the affinity substance dissolved in the solution from free affinity substance by using an ultrafiltration membrane having an ability to retain the complex having a molecular weight of about 1.2 times or more as large as that of the affinity substance in solution remaining above the ultrafiltration membrane without dissociating the complex and allow the free affinity substance to pass through, measuring the amount of the labeling substance in the resulting complex or in the free affinity substance in a filtrate, and measuring the mount of analyte using a calibration curve showing a relationship between the amount of analyte and the amount of labeling substance, wherein the analyte to be measured is a saccharide or a lectin, and the affinity substance is a lectin or saccharide, respectively, suitable for the analyte.

2. A process for measuring the amount of an analyte in a sample which comprises mixing a sample containing an analyte to be measured with the analyte which has been labeled with a labeling substance and an affinity substance having affinity for the analyte, allowing the unlabeled analyte and the labeled analyte to form complexes with the affinity substance, said complexes being dissolved in solution and having a molecular weight of about 1.2 times or more as large as that of the affinity substance and having a tendency to be dissociated into the unlabeled and labeled analyte and the affinity substance due to weak interaction, separating the resulting complex of the labeled analyte and the affinity substance dissolved in the solution from free labeled analyte by using an ultrafiltration membrane having an ability to retain the complex having a molecular weight of about 1.2 times or more as large as that of the affinity substance in solution remaining above the ultrafiltration membrane without dissociating the complex and allow the free labeled analyte to pass through, measuring the amount of the labeling substance in the resulting complex or in the free labeled analyte in a filtrate, and measuring the amount of analyte using a calibration curve showing a relationship between the amount of analyte and the amount of labeling substance, wherein the analyte to be measured is a saccharide or a lectin, and the affinity substance is a lectin or saccharide, respectively, suitable for the analyte.

3. A process for measuring the amount of a saccharide in a sample which comprises, mixing a sample containing a saccharide to be measured with a lectin having affinity for the saccharide labeled with a labeling substance, allowing the saccharide to form a complex with the lectin, said complex being dissolved in solution and having a molecular weight of about 1.2 times or more as large as that of the lectin and having a tendency to be dissociated into the saccharide and the lectin due to weak interaction, separating the resulting complex of the saccharide and the lectin dissolved in the solution from the free lectin by using a membrane having an ability to retain the complex having a molecular weight of about 1.2 times or more as large as that of the affinity substance in solution remaining above the ultrafiltration membrane without dissociating the complex and allow the free lectin to pass through, measuring the amount of the labeling substances in the complex or in the free lectin in a filtrate, and measuring the amount of the saccharide using a calibration curve showing a relationship between the amount of saccharide and the amount of the labeling substance.

4. A process for measuring the amount of saccharide in a sample which comprises, mixing a sample containing a saccharide to be measured with the saccharide which has been labeled with a labeling substance and a lectin having affinity for the saccharide, allowing the unlabeled saccharide and the labeled saccharide to form a complex with the lectin, said complex being dissolved in a solution and having a molecular weight of about 1.2 times or more as large as that of the lectin, and having a tendency to be dissociated into the unlabeled and labeled saccharide and the lectin due to weak interaction, separating the resulting complex of the labeled saccharide and the lectin dissolved in the solution from the free labeled saccharide by using a membrane having an ability to retain the complex having a molecular weight of about 1.2 times or more as large as that of the affinity substance in solution remaining above the ultrafiltration membrane without dissociating the complex and allow the free labeled saccharide to pass through, measuring the amount of the labeling substance in the resulting complex or in the free labeled saccharide in a filtrate, and measuring the amount of the saccharide using a calibration curve showing a relationship between the amount of saccharide and the amount of the labeling substance.

5. A process for separating a complex of a saccharide to be measured and a lectin having affinity for the saccharide from the free lectin, the complex having a molecular weight of about 1.2 times or more as large as that of the lectin, which comprises, separating the complex having a tendency to be dissociated into the saccharide and the lectin due to weak interaction, and dissolved in a solution from the free lectin by using a membrane having an ability to retain the complex having a molecular weight of about 1.2 times or more as large as that of the affinity substance in solution remaining above the ultrafiltration membrane without dissociating the complex and allow the free lectin to pass through, said complex being formed by mixing a sample containing the saccharide with the lectin labeled with a labeling substance, thereby reacting the saccharide with the lectin, said complex being dissolved in the solution.

6. A process for separating a complex of saccharide to be measured which has been labeled with labeling substance and a lectin having affinity for the saccharide from the labeled saccharide, the complex having a molecular weight of about 1.2 times or more as large as that of the lectin, which comprises, separating the labeled complex having a tendency to be dissociated into the labeled saccharide and the lectin due to weak interaction, and dissolved in a solution from the free labeled saccharide by using a membrane having an ability to retain the complex having a molecular weight of about 1.2 times or more as large as that of the affinity substance in solution remaining above the ultrafiltration membrane without dissociating the complex and allow the free labeled saccharide to pass through, said complex being formed by mixing a sample containing the saccharide with the labeled saccharide and the lectin, thereby reacting the unlabeled saccharide and the labeled saccharide with the lectin, said complex being dissolved in the solution.

7. A process for measuring the amount of a lectin in a sample which comprises, mixing a sample containing a lectin to be measured with saccharide having affinity for the lectin labeled with a labeling substance, allowing the lectin to form a complex with the saccharide, said complex being dissolved in solution and having a molecular weight of about 1.2 times or more as large as that of the saccharide and having a tendency to be dissociated into the lectin and the saccharide due to weak interaction, separating the resulting complex of the lectin and saccharide dissolved in the solution from the free saccharide by using a membrane having an ability to retain the complex having a molecular weight of about 1.2 times or more as large as that of the affinity substance in solution remaining above the ultrafiltration membrane without dissociating the complex and allow the free saccharide to pass through, measuring the amount of the labeling substance in the complex or in the free saccharide in a filtrate, and measuring the amount of lectin using a calibration curve showing a relationship between the amount of lectin and the amount of the labeling substance.

8. A process for measuring the amount of a lectin in a sample which comprises, mixing a sample containing a lectin to be measured with the lectin which has been labeled with a labelling substance and a saccharide having affinity for the lectin, allowing the lectin and the labeled lectin to form a complex with the saccharide, said complex being dissolved in solution and having a molecular weight of about 1.2 times or more as large as that of the saccharide and having a tendency to be dissociated into the unlabeled and labeled lectin and the saccharide due to weak interaction, separating the resulting complex of the labeled lectin and the saccharide dissolved in the solution from the free labeled lectin by using a membrane having an ability to retain the complex having a molecular weight of about 1.2 times or more as large as that of the affinity substance in solution remaining above the ultrafiltration membrane without dissociating the complex and allow the free labeled lectin to pass through, measuring the amount of the labeling substance in the resulting complex or in the free labeled lectin in a filtrate, and measuring the amount of lectin using a calibration curve showing a relationship between the amount of lectin and the amount of the labeling substance.

9. A process for separating a complex of a lectin to be measured and a saccharide having affinity for the lectin from the free saccharide, the complex having a molecular weight of about 1.2 times or more as large as that of the saccharide, which comprises, separating the complex having a tendency to be dissociated into the lectin and the saccharide due to weak interaction dissolved in a solution from the free saccharide by using a membrane having an ability to retain the complex having a molecular weight of about 1.2 times or more as large as that of the affinity substance in solution remaining above the ultrafiltration membrane without dissociating the complex and allow the free saccharide to pass through, said complex being formed by mixing a sample containing the lectin with the saccharide labeled with a labeling substance, thereby reacting the lectin with the saccharide, said complex being dissolved in the solution.

10. A process for separating a complex of a lectin to be measured which has been labeled with labeling substance and a saccharide having affinity for the lectin from the labeled lectin the complex having a molecular weight of about 1.2 times or more as large as that of the saccharide, which comprises, separating the labeled complex having a tendency to be dissociated into the labeled lectin and the saccharide due to weak interaction, and dissolved in a solution from the free labeled lectin by using a membrane having an ability to retain the complex having a molecular weight of about 1.2 times or more as large as that of the affinity substance in solution remaining above the ultrafiltration membrane without dissociating the complex and allow the free labeled lectin to pass through, said complex being formed by mixing a sample containing the lectin with the labeled lectin and the saccharide, thereby reacting the unlabeled lectin and the labeled lectin with the saccharide, the complex being dissolved in the solution.

* * * * *